United States Patent
Kawai et al.

(10) Patent No.: US 11,964,034 B2
(45) Date of Patent: Apr. 23, 2024

(54) DOUBLE-STRUCTURED STICK COSMETIC AND MANUFACTURING METHOD THEREOF

(71) Applicant: TOKIWA CORPORATION, Nakatsugawa (JP)

(72) Inventors: Seiji Kawai, Kawaguchi (JP); Yoshinori Akamatsu, Kawaguchi (JP)

(73) Assignee: TOKIWA CORPORATION, Nakatsugawa (JP)

( * ) Notice: Subject to any disclaimer, the term of this patent is extended or adjusted under 35 U.S.C. 154(b) by 0 days.

(21) Appl. No.: 17/881,991

(22) Filed: Aug. 5, 2022

(65) Prior Publication Data

US 2023/0053578 A1 Feb. 23, 2023

(30) Foreign Application Priority Data

Aug. 6, 2021 (JP) ................. 2021-129913

(51) Int. Cl.
*A61K 8/02* (2006.01)
*A61K 8/891* (2006.01)
*A61Q 1/04* (2006.01)
*A61Q 1/10* (2006.01)

(52) U.S. Cl.
CPC ............ *A61K 8/0229* (2013.01); *A61K 8/891* (2013.01); *A61Q 1/04* (2013.01); *A61Q 1/10* (2013.01); *A61K 2800/805* (2013.01); *A61K 2800/872* (2013.01)

(58) Field of Classification Search
None
See application file for complete search history.

(56) References Cited

U.S. PATENT DOCUMENTS

2020/0268639 A1 * 8/2020 Kokai ..................... A61K 8/29

FOREIGN PATENT DOCUMENTS

| JP | H0733324 | B2 | * | 6/1988 |
| JP | S63-139107 | A | | 6/1988 |
| JP | 2008-133205 | A | | 6/2008 |
| JP | 2012-077049 | A | | 4/2012 |
| JP | 2017-095452 | A | | 6/2017 |
| WO | WO 2013/065767 | | * | 5/2013 |

* cited by examiner

*Primary Examiner* — Danah Al-Awadi
(74) *Attorney, Agent, or Firm* — Procopio, Cory, Hargreaves & Savitch LLP

(57) ABSTRACT

A double-structured stick cosmetic includes a solid-form outer layer containing a first oil composition, and an inner core containing a second oil composition, in which the first oil composition contains (A) an alkyl-modified silicone having an alkyl group having 16 to 50 carbon atoms and (B) a wax in a solid-form at 25° C. other than (A). The component (A) may have a melting point of 25° C. or higher and 50° C. or lower. A mass ratio [(A)/(B)] of the component (A) to the component (B) contained in the first oil composition may be 0.2 or larger and 1.5 or smaller.

19 Claims, No Drawings

DOUBLE-STRUCTURED STICK COSMETIC AND MANUFACTURING METHOD THEREOF

CROSS-REFERENCE TO RELATED APPLICATIONS

This application is based on and claims priority under 35 USC 119 from Japanese Patent Application No. 2021-129913 filed on Aug. 6, 2021, the contents of which are incorporated herein by reference.

TECHNICAL FIELD

The present invention relates to a double-structured stick cosmetic and a manufacturing method thereof.

BACKGROUND ART

Stick cosmetics such as an eyeliner, an eyebrow pencil, a lipliner, a concealer pencil, and an eye shadow pencil are used in the form of a pencil or a mechanical pencil cosmetic applicator used by screwing a lead out. Examples of the performance desired to such cosmetics include smoothness when drawing, color development, usability such as a long-lasting effect, and impact resistance that the writing-core is not broken when carried while having a fine core diameter suitable for an application portion.

The stick cosmetic generally contains a solid-form oil such as wax, a liquid-form oil, and a powder such as a pigment, as a framework. A mechanical strength such as the impact resistance or moldability when manufacturing, and the usability are controlled by a mixing ratio of the solid-form oil and the liquid-form oil, but it is extremely difficult to satisfy both of the mechanical strength and the usability simultaneously. In the case of increasing the amount of wax to increase the mechanical strength, the smoothness when drawing or the long-lasting effect is degraded, whereas in the case of decreasing the amount of wax, the mechanical strength is degraded. Various studies have been conducted in order to make the mechanical strength and the usability compatible (refer to Patent Literatures 1 and 2). However, in such technologies, it was not sufficient to make the mechanical strength and the usability such as the smoothness when drawing compatible.

A stick cosmetic has been known in which the performance that is difficult to attain with a single phase is established by a double structure having different compositions or by a divided structure including a plurality of layers (refer to Patent Literatures 3 and 4).

[Patent Literature 1] JP-A-2012-77049
[Patent Literature 2] JP-A-2008-133205
[Patent Literature 3] JP-A-S63-139107
[Patent Literature 4] JP-A-2017-95452

SUMMARY OF INVENTION

In the technology of the stick cosmetic having a double structure, an inner core composition having a low hardness imparts a feeling of use such as the smoothness, and a solid-form outer layer portion retains the impact resistance or the shape retainability. Since such a conventional technology is for lip cosmetics such as a lipstick, the core diameter is large for eye cosmetics, and double-structured stick cosmetics having a fine core diameter that is suitable for an eyeliner or the like has not been proposed yet. In general, if the area of the inner core is increased by giving priority to the feeling of use, the area of the outer layer portion decreases and the mechanical strength is not capable of being satisfied. On the other hand, if the thickness of the outer layer is increased by giving priority to the mechanical strength, the feeling of use is degraded. Therefore, it is difficult to make the mechanical strength and the feeling of use compatible, especially in the case of a fine core diameter.

Even in a manufacturing procedure, in the case where the writing-core has an elongated shape and the outer layer is thin, there is a problem in the shape retainability when manufacturing in which a double-structured stick cosmetic in a state of being filled with the inner core is likely to collapse when released from a mold. In particular, in the case where the inner core is not a solid-form but in the form of a semi-solid-form or a paste-form, it is more difficult to retain the shape.

Therefore, an object of the present invention is to provide a double-structured stick cosmetic that has sufficient shape retainability when manufacturing and is excellent in smoothness when drawing and impact resistance, and a manufacturing method thereof.

As a result of intensive studies of the present inventors to attain the object described above, they found that in a double-structured stick cosmetic including a solid-form outer layer containing an oil composition and an inner core containing another oil composition in which the composition of the outer layer is obtained by combining and blending a specific alkyl-modified silicone with a wax in a solid-form at 25° C., even in the case of an elongated stick cosmetic, shape retainability when manufacturing is excellent regardless of the form of the inner core, and smoothness when drawing and impact resistance can be obtained. They completed the present invention base on the findings.

That is, the present invention provides a double-structured stick cosmetic, including: a solid-form outer layer containing a first oil composition; and an inner core containing a second oil composition, in which the first oil composition contains (A) an alkyl-modified silicone having an alkyl group having 16 to 50 carbon atoms and (B) a wax in a solid-form at 25° C. other than (A).

It is preferable that in the double-structured stick cosmetic of the present invention, the component (A) has a melting point of 25° C. or higher and 50° C. or lower. The use of the alkyl-modified silicone wax having a specific melting point makes it possible to obtain smoothness when drawing, excellent impact resistance, and shape retainability when manufacturing.

It is preferable that in the double-structured stick cosmetic of the present invention, a mass ratio [(A)/(B)] of the component (A) to the component (B) contained in the first oil composition is 0.2 or larger and 1.5 or smaller, from the viewpoint of making usability and the impact resistance compatible in a high level.

It is preferable that in the double-structured stick cosmetic of the present invention, a diameter is 1 mm or larger and 7 mm or smaller, from the viewpoint of ease of drawing when drawing a fine line around the eyes such as on the eyelids.

In addition, the present invention provides a manufacturing method of a double-structured stick cosmetic including an inner core and a solid-form outer layer, the method including steps of: placing a stick-shaped inner mold inside a tubular mold; filling a gap between the stick-shaped inner mold and the tubular mold with a first oil composition; solidifying the first oil composition; removing the stick-shaped inner mold to form the outer layer having a cavity inside; filling the cavity with a second oil composition to form the inner core; and taking out the double-structured stick cosmetic including the inner core and the outer layer from the tubular mold, in which the first oil composition contains (A) an alkyl-modified silicone having an alkyl group having 16 to 50 carbon atoms and (B) a wax in a solid-form at 25° C. other than (A).

According to the present invention, it is possible to provide a double-structured stick cosmetic that is excellent in shape retainability when manufacturing, and has smoothness when drawing and excellent impact resistance, and also possible to provide a manufacturing method thereof.

DESCRIPTION OF EMBODIMENTS

A double-structured stick cosmetic of this embodiment contains a solid-form outer layer containing an oil composition (first oil composition), and an inner core containing another oil composition (second oil composition), and the first oil composition of the outer layer contains (A) an alkyl-modified silicone having an alkyl group having 16 to 50 carbon atoms (hereinafter, may be referred to as a component (A)), and (B) a wax in a solid-form at 25° C. other than (A) (hereinafter, may be referred to as a component (B)). The term "double-structured" used herein means that the stick cosmetic contains the solid-form outer layer and the inner core as main and essential components and does not exclude additional layer so long as it does not impair the effect of the present invention. The double-structured stick cosmetic of this embodiment may contain another layer in addition to the outer layer and the inner core, as the outermost layer or as an intermediate layer between the outer layer and the inner core.

In the present invention, the solid-form outer layer containing the first oil composition may be referred to as an outer layer composition, and the inner core containing the second oil composition may be referred to as an inner core composition.

In the present invention, the term "solid-form" indicates a state where fluidity is not exhibited at a room temperature (25° C.) and there is no deformation by an external force.

The oil composition of the inner core may be in the form of a solid-form, a semi-solid-form, a paste-form, or a gel-form at 25° C.

<(A) Alkyl-Modified Silicone Having Alkyl Group Having 16 to 50 Carbon Atoms>

The alkyl-modified silicone is silicone having an alkyl group, and the alkyl group may be substituted on any one of a side chain, one terminal, and both terminals of a polysiloxane chain, and is more preferably substituted on the side chain from the viewpoint of shape retainability when manufacturing and impact resistance. The alkyl group is preferably a straight chain or a branched chain having 16 to 50 carbon atoms, more preferably a straight chain or a branched chain having 18 to 30 carbon atoms, and even more preferably a straight chain or a branched chain having 24 to 28 carbon atoms.

Examples of the alkyl-modified silicone of the component (A) include stearyl dimethicone, alkyl (C26-28) dimethicone, bisstearoxydimethyl silane, and the like, and commercially available products such as 2503 Cosmetic WAX (manufactured by Dow Corning Toray Co., Ltd., Product Name), BELSIL SDM 5055VP (manufactured by Wacker Asahikasei Silicone Co., Ltd., Product Name), BELSIL CDM 3526VP (manufactured by Wacker Asahikasei Silicone Co., Ltd., Product Name), BELSIL W3230 (manufactured by Wacker Asahikasei Silicone Co., Ltd., Product Name), and SF1632 (manufactured by Momentive Performance Materials Inc., Product Name) can be used.

In the double-structured stick cosmetic of this embodiment, the component (A) has a melting point of preferably 25° C. or higher, more preferably 30° C. or higher, and even more preferably 35° C. or higher, and is preferably 60° C. or lower, more preferably 50° C. or lower, and even more preferably 45° C. or lower, from the viewpoint of making smoothness when drawing and the impact resistance compatible.

In this description, the melting point indicates a value that is measured by the following method. Approximately 5 mg of a sample is weighed and put in an aluminum sample pan. An aluminum cover is attached to the pan, and the pan is placed in a differential scanning calorimeter "DSC7020" (manufactured by Hitachi High-Tech Science Corporation, Product Name). The sample and a reference sample are retained at −10° C. for 1 minute at a nitrogen gas flow rate of 30 mL/min to 50 mL/min by using an electric cooling unit "Polyscience" (manufactured by Hitachi High-Tech Science Corporation, Product Name), and then, are heated to 100° C. from −10° C. at a temperature increase rate of 10° C./min, are cooled to −10° C. from 100° C. at a temperature decrease condition of −10° C./min, and are heated again to 100° C. from −10° C. at a temperature increase rate of 10° C./min, whereby a melting endothermic curve is obtained. At this time, a peak temperature of the melting endothermic curve in the second temperature increase is adopted as the melting point. In the case where there are a plurality of peak temperatures, a peak temperature having the highest melting temperature is set as the melting point.

In addition, it is preferable that the component (A) does not exhibit the fluidity at 25° C. and is in the form of a semi-solid-form or a paste-form, from the viewpoint of the smoothness when drawing. In the present invention, the term "semi-solid-form" indicates a state where fluidity is not exhibited at a room temperature (25° C.) and the melting point falls in the range of 25° C. to 60° C.

As the component (A), one type can be used alone, or two or more types can be used in combination.

The content of the component (A) in the outer layer composition is preferably 1% by mass or more, more preferably 3% by mass or more, and even more preferably 5% by mass or more, and is preferably 15% by mass or less, more preferably 13% by mass or less, and even more preferably 10% by mass or less, on the basis of the total amount of the outer layer composition. In the case where the content is 1% by mass or more, the shape retainability when manufacturing is more excellent regardless of the properties of the inner core composition, and in the case where the content is 15% by mass or less, it is possible to impart the more excellent smoothness when drawing while maintaining the impact resistance.

The inner core composition of this embodiment may or may not contain the component (A), and preferably contains the component (A) from the viewpoint of the impact resistance and the shape retainability when manufacturing. The content of the component (A) in the inner core composition is preferably 0.1% by mass or more, more preferably 3% by mass or more, and even more preferably 5% by mass or more, and is preferably 15% by mass or less, more preferably 10% by mass or less, and even more preferably 8% by mass or less, on the basis of the total amount of the inner core composition.

<(B) Wax in a Solid-Form at 25° C. Other than Component (A)>

The component (B) is wax in a solid-form at 25° C., and is not particularly limited insofar as it is wax that is generally used in cosmetics. Specifically, examples of the component (B) include hydrocarbon waxes such as polyethylene wax, paraffin wax, ceresin wax, microcrystalline wax, an ethylene-propylene copolymer, Fischer-Tropsch wax, synthetic wax, polypropylene wax, montan wax, and ozocerite wax, plant waxes such as carnauba wax, candelilla wax, Japan wax, rice bran wax, and sunflower wax, animal waxes such as yellow beeswax and spermaceti wax, esters such as glyceryl tribehenate and cholesterol fatty acid ester, higher fatty acids such as a stearic acid and a behenic acid, higher alcohols such as stearyl alcohol and behenyl alcohol, silicone waxes such as an alkyl-modified silicone other than the component (A), and an acrylic-modified silicone, and the like. One type of the above can be used alone, or two or more types thereof can be used in combination.

As the component (B), only one type may be used, or two or more types may be used in combination. Among them, in the case where the component (B) is contained in the outer layer composition, wax having a melting point of 65° C. or higher is preferable from the viewpoint of the shape retainability when manufacturing and the impact resistance. Examples of such wax include candelilla wax, rice bran wax, yellow beeswax, polyethylene wax, and the like, and among them, the polyethylene wax and the candelilla wax are preferable from the viewpoint of the shape retainability when manufacturing.

The content of the component (B) in the outer layer composition is preferably 5% by mass or more, more preferably 6% by mass or more, and even more preferably 8% by mass or more, and is preferably 20% by mass or less, more preferably 16% by mass or less, and even more preferably 14% by mass or less, on the basis of the total amount of the outer layer composition. In the case where the content is 5% by mass or more, it is possible to maintain the shape retainability when manufacturing and the impact resistance more effectively. In the case where the content is 20% by mass or less, it is possible to maintain the smoothness when drawing more effectively.

The inner core composition of this embodiment may contain the component (B). The content of the component (B) in the inner core composition is preferably 0.1% by mass or more, more preferably 1% by mass or more, and even more preferably 3% by mass or more, from the viewpoint of the smoothness when drawing, and is preferably 15% by mass or less, more preferably 13% by mass or less, and even more preferably 10% by mass or less, on the basis of the total amount of the inner core composition.

A mass ratio [(A)/(B)] of the component (A) to the component (B) in the outer layer composition is preferably 0.2 or more, more preferably 0.3 or more, and even more preferably 0.4 or more, and is preferably 2.0 or less, more preferably 1.6 or less, and even more preferably 1.0 or less, from the viewpoint of making the smoothness when drawing and the impact resistance compatible. Here, each of the masses of the component (A) and the component (B) in the outer layer composition is a mass based on the total amount of the outer layer composition.

A mass ratio [(A)/(B)] of the component (A) to the component (B) in the inner core composition is preferably 0.2 or more, more preferably 0.5 or more, and even more preferably 1.0 or more, and is preferably 2.0 or less, more preferably 1.6 or less, and even more preferably 1.4 or less, from the viewpoint of the smoothness when drawing. Here, each of the masses of the component (A) and the component (B) in the inner core composition is a mass based on the total amount of the inner core composition.

The stick cosmetic of this embodiment may further contain a volatile oil agent, an oil agent other than the component (A) and the component (B), an oil thickener, a film-forming agent, a powder, and other components, as necessary. One type of such components may be contained alone, or two or more types thereof may be contained in combination.

Examples of the volatile oil agent include isododecane, dodecane, (C9-12) alkane, light isoparaffin, disiloxane, trisiloxane, methyl trimethicone, dimethicone (1 to 2 cs), cyclotetrasiloxane, cyclopentasiloxane, cyclohexasiloxane, and the like. The volatile oil agent indicates an oil agent having a boiling point of 250° C. or lower at 1 atm (101.325 kPa).

The content of the volatile oil agent in the outer layer composition is preferably 5% by mass or more, more preferably 10% by mass or more, and even more preferably 15% by mass or more, from the viewpoint of a feeling of use, and is preferably 50% by mass or less, more preferably 45% by mass or less, and even more preferably 35% by mass or less, on the basis of the total amount of the outer layer composition.

The content of the volatile oil agent in the inner core composition is preferably 0.1% by mass or more, more preferably 5% by mass or more, and even more preferably 10% by mass or more, and is preferably 80% by mass or less, more preferably 60% by mass or less, and even more preferably 50% by mass or less, on the basis of the total amount of the inner core composition.

In the stick cosmetic of this embodiment, as the oil agent other than the component (A) and the component (B), a paste-form oil, a liquid-form oil or the like can be used without being particularly limited insofar as it is an oil agent that is generally used in cosmetics. As the oil agent, one type can be used alone, or two or more types can be used in combination. Such an oil agent does not exhibit volatility.

Examples of the paste-form oil include vaseline, dipentaerythrityl hexa(hydroxystearate/stearate/rosinate), dipentaerythrityl tetra(hydroxystearate/isostearate), dipentaerythrityl pentaisostearate, dipentaerythrityl hexahydroxystearate, glyceryl tri(caprylate/caprate/myristate/stearate), hydrogenated castor oil isostearate, phytosteryl oleate, sucrose hexa(oleate/palmitate/stearate), bis(behenyl/isostearyl/phytosteryl) dimer dilinoleyl dimer dilinoleate, (phytosteryl/isostearyl/cetyl/stearyl/behenyl) dimer dilinoleyl, hydrogenated castor oil dimer dilinoleyl, macadamia nut fatty acid phytosteryl ester, bisdiglyceryl polyacyl adipate-2, and the like.

Examples of the liquid-form oil include ester oils such as cetyl ethyl hexanoate, hexyl ethyl palmitate, triethyl hexanoin, isotridecyl isononanoate, isostearyl isostearate, neopentyl glycol diethyl hexanoate, glyceryl tri(caprylate/caprate), neopentyl glycol dicaprate, propanediol diisostearate, trimethylol propane triethyl hexanoate, octyl dodecyl myristate, octyl dodecyl stearoyl oxystearate, diisostearyl malate, polyglyceryl triisostearate, dipentaerythrityl pentaisostearate, and trimethylol propane triisostearate, silicone oils such as dimethicone and methyl phenyl polysiloxane, hydrocarbon oils such as liquid paraffin, an olefin oligomer, squalane, and hydrogenated polyisobutene, plant oils such as sunflower seed oil, jojoba seed oil, olive oil, and castor oil, higher alcohols such as isostearyl alcohol, octyl dodecanol, and oleyl alcohol, and the like.

The content of the oil agent other than the component (A) and the component (B) in the outer layer composition is preferably 0.1% by mass or more, more preferably 0.5% by mass or more, and even more preferably 1% by mass or more, and is preferably 20% by mass or less, more preferably 10% by mass or less, and even more preferably 5% by mass or less, on the basis of the total amount of the outer layer composition.

In the case where the inner core composition is in the form of a solid-form, the content of the oil agent other than the component (A) and the component (B) in the inner core composition is preferably 0.1% by mass or more, more preferably 0.5% by mass or more, and even more preferably 1% by mass or more, and is preferably 20% by mass or less, more preferably 10% by mass or less, and even more preferably 5% by mass or less, on the basis of the total amount of the inner core composition. In the case where the inner core composition is in the form of a paste-form or a semi-solid-form, the content of the oil agent other than the component (A) and the component (B) in the inner core composition is preferably 1% by mass or more, more preferably 10% by mass or more, and even more preferably 20% by mass or more, and is preferably 80% by mass or less, more preferably 60% by mass or less, and even more preferably 50% by mass or less, on the basis of the total amount of the inner core composition.

The stick cosmetic of this embodiment may contain the film-forming agent from the viewpoint of long-lasting properties, and examples of the film-forming agent include a silicone film-forming agent such as trimethyl siloxysilicate, polypropyl silsesquioxane, polymethyl silsesquioxane, polyphenyl silsesquioxane, and a (polytrimethyl siloxy acrylate/methacrylate) copolymer, and a terpene film-forming agent such as a candelilla resin, and pentaerythritol rosinate. Among them, the trimethyl siloxysilicate is preferable from the viewpoint of making the shape retainability when released from a mold and the impact resistance and the long-lasting properties compatible. The film-forming agent may be dispersed in advance in a liquid-formed oil or the like.

The content of the film-forming agent in the outer layer composition is preferably 5% by mass or more, more preferably 10% by mass or more, and even more preferably 15% by mass or more, and is preferably 50% by mass or less, more preferably 40% by mass or less, and even more preferably 30% by mass or less, on the basis of the total amount of the outer layer composition.

The content of the film-forming agent in the inner core composition is preferably 1% by mass or more, more preferably 10% by mass or more, and even more preferably 15% by mass or more, and is preferably 50% by mass or less, more preferably 40% by mass or less, and even more preferably 30% by mass or less, on the basis of the total amount of the inner core composition.

The stick cosmetic of this embodiment may contain the oil thickener. The oil thickener can be used without being particularly limited insofar as it is an oil thickener that is generally used in cosmetics. One type of oil thickener can be used alone, or two or more types can be used in combination.

Examples of the oil thickener include partially crosslinked organopolysiloxanes such as a dimethicone crosspolymer, a (dimethicone/vinyl dimethicone) crosspolymer, a (dimethicone/phenyl vinyl dimethicone) crosspolymer, a (vinyl dimethicone/lauryl dimethicone) crosspolymer, and a (dimethicone/vinyl trimethyl siloxysilicate) crosspolymer, dextrin fatty acid esters such as dextrin palmitate, dextrin palmitate/2-ethyl hexanoate, dextrin stearate, dextrin palmitate/stearate, dextrin oleate, dextrin isopalmitate, and dextrin isostearate, sucrose fatty acid esters such as sucrose stearate and sucrose stearate acetate, inulin stearates, starch fatty acid esters, metallic soaps such as aluminum isostearate, calcium stearate, aluminum stearate, magnesium stearate, aluminum myristate, and magnesium myristate, oil gellants such as dibutyl ethyl hexanoyl glutamide and dibutyl lauroyl glutamide, natural or synthetic montmorillonite groups such as montmorillonite, saponite, bentonite, and hectorite, and organic-modified clay minerals obtained by treating a clay mineral such as sodium silicic mica or synthetic mica known as sodium taeniolite or lithium taeniolite with a quaternary ammonium salt cationic surfactant.

The inner core composition of the stick cosmetic of this embodiment may be a composition in the form of a paste-form or a gel-form containing the oil agent, the volatile oil agent, and the oil thickener, from the viewpoint of imparting various feelings of use. In the case where the inner core composition is in the form of a paste-form or a gel-form, the content of the oil thickener in the inner core composition is preferably 1% by mass or more, more preferably 5% by mass or more, and even more preferably 7% by mass or more, and is preferably 30% by mass or less, more preferably 27% by mass or less, and even more preferably 25% by mass or less, on the basis of the total amount of the inner core composition.

The powder can be used without being particularly limited insofar as it is a powder that is generally used in cosmetics, and examples of the powder include extender powders, pigments (e.g., color pigments), and the like. As the powder, powders in the shape of a sphere, a plate, a needle, and the like; powders having a particle diameter of haze particles, fine particles, pigment grade particles, and the like; and powders having a porous structure and a non-porous structure can be used without being particularly limited. Examples of the powder include inorganic color pigments such as black iron oxide, colcothar, yellow iron oxide, cobalt oxide, chromium oxide, ultramarine blue, iron blue, titanium oxide, zinc oxide, and carbon black, organic color pigments such as Red No. 228, Red No. 226, Blue No. 404, Red No. 202, and Yellow No. 4 aluminum lakes, pearl pigments such as titanated mica, argentine, and bismuth oxychloride, natural dyes such as carnine and safflower, extender pigments such as a glass powder, silicic anhydride, aluminum silicate, magnesium silicate, aluminum magnesium silicate, mica, synthetic mica, synthetic sericite, sericite, talc, kaolin, silicon carbide, and barium sulfate, spherical powders such as cross-linked polymethyl methacrylate and a silicone elastomer, and the like. As the powder, only one type may be used, or two or more types may be used in combination. In addition, as necessary, the powder may be subjected to a surface treatment by a known method using a fluorine compound, a silicone compound, a metallic soap, lecitin, hydrogenated lecitin, collagen, a hydrocarbon, a higher fatty acid, a higher alcohol, an ester, wax, a surfactant, and the like, or may be further compounded.

The content of the powder in the outer layer composition is preferably 10% by mass or more, more preferably 15% by mass or more, and even more preferably 20% by mass or more, and is preferably 50% by mass or less, more preferably 45% by mass or less, and even more preferably 40% by mass or less, on the basis of the total amount of the outer layer composition. In the case where the content is less than 10% by mass, color development may be insufficient as cosmetics, and in the case where the content is greater than 50% by mass, a stick cosmetic with poor elongation properties may be obtained.

The content of the powder in the inner core composition is preferably 1% by mass or more, more preferably 5% by mass or more, and even more preferably 10% by mass or more, and is preferably 60% by mass or less, more preferably 50% by mass or less, and even more preferably 40% by mass or less, on the basis of the total amount of the inner core composition.

The stick cosmetic of this embodiment is capable of containing components that are generally used in cosmetics, for example, an antiseptic agent, an antioxidant, a dye, a pH adjuster, a perfume, an ultraviolet absorber, an ultraviolet scattering agent, a moisturizer, a chelate agent, an antiphlogistic, and the like, in addition to the components described above.

A bulk hardness of the outer layer of the stick cosmetic according to this embodiment is preferably 0.5 N or more, and more preferably 0.8 N or more, and is preferably 2.5 N or less, more preferably 2.0 N or less, and even more preferably 1.5 N or less, from the viewpoint of the impact resistance and moldability. In the case where the bulk hardness of the outer layer is in the range described above, excellent moldability may be obtained, and the impact resistance and the feeling of use can be compatible at higher level.

A bulk hardness of the inner core of the stick cosmetic according to this embodiment is preferably 0.01 N or more, and more preferably 0.1 N or more, and is preferably 1.0 N or less, more preferably 0.6 N or less, and even more preferably 0.5 N or less, from the viewpoint of making the impact resistance or the moldability and the feeling of use compatible. In the case where the bulk hardness of the inner core is 0.01 N or more, further smoothness that is not capable of being felt with single-layer stick cosmetics can be felt when drawing.

A ratio of the bulk hardness of the inner core to the bulk hardness of the outer layer is preferably 0.05 or more, more preferably 0.15 or more, and even more preferably 0.2 or more, from the viewpoint of the impact resistance and the feeling of use, and is preferably 0.8 or less, more preferably 0.6 or less, and even more preferably 0.5 or less. In the case where the ratio of the bulk hardness is 0.05 or more, a feeling of unity when using the outer layer composition and the inner layer composition can be imparted more efficiently, and in the case where the ratio of the bulk hardness is 0.8 or less, further smoothness that is not capable of being felt with single-layer stick cosmetics can be felt when drawing.

The bulk hardness indicates the maximum value of a penetration of a needle, which is obtained by measuring a sample of a stick cosmetic in conditions of a pressure-sensitive axis of 1 mmϕ, a penetration rate of 6 cm/min, and a penetration depth of 10 mm, by using FUDOH Rheo Meter RT-2002D•D (manufactured by RHEOTECH). The sample is prepared by filling a screw cap container (Volume: 30 mL) with the cosmetic that is melted by heating or dissolved in a volatile solvent, and by leaving the cosmetic at 25° C. overnight to be solidified.

The double-structured stick cosmetic of this embodiment can be manufactured by blending the components described above, in accordance with a known method. Examples of the known method include a method of placing a stick-shaped inner mold inside a tubular mold; filling a gap between the stick-shaped inner mold and the tubular mold with a first oil composition; solidifying the first oil composition; removing the stick-shaped inner mold to form the outer layer having a cavity inside; filling the cavity with a second oil composition to form the inner core; and taking out the double structure stick cosmetic including the inner core and the outer layer from the tubular mold. The first oil composition that is to be the outer layer may be heated and melted to fill the gap. The melted first oil composition can be solidified by cooling. A configuration ratio of the outer layer and the inner core can be adjusted by changing the size of the stick-shaped inner mold and the tubular mold. In the cross-section in a direction perpendicular to the longitudinal direction of the stick cosmetic, the tubular mold may be concentric or eccentric with the stick-shaped inner mold.

The outer layer composition and the inner core composition can be prepared by mixing, heating, and dissolving the component (A), the component (B), and as necessary, other components, and the like. For example, a precursor composition containing the component (B) may be heated to the melting point or higher of the component (B), to the melt may be mixed a powder component(s), and the obtained mixture is homogeneously dispersed by a triple roller or a stirrer. After that, the volatile oil agent, the film-forming agent, or as necessary, other components may be mixed and stirred therein, whereby a homogeneous composition can be obtained.

The stick cosmetic of this embodiment is a double-structured stick cosmetic in which the outside of the inner core composition is covered with the outer layer composition. The lateral surface of the inner core may be completely or partially covered with the outer layer composition. The covering ratio of the inner core composition by the outer layer composition is preferably 60% or more, more preferably 80% or more, and further preferably 100% (completely covered). The upper surface (writing-side surface) of the inner core may be completely or partially covered with the outer layer, and the inner core may be completely exposed to the surface.

The stick cosmetic of this embodiment is preferable for stick cosmetics that are used in a stick cosmetic product used by extruding a writing-core or an elongated cosmetic product such as a pencil cosmetic product. The sectional surface of the stick cosmetic in a direction perpendicular to the longitudinal direction of the stick cosmetic may be in the shape of a circle, an ellipse, a droplet, a rectangle, or the like without being particularly limited. Since the stick cosmetic is applied to the soft skin (e.g., around the eyes), it is preferable that the sectional surface is in the shape of a circle or an ellipse. The sectional surface of the inner core in the direction perpendicular to the longitudinal direction of the stick cosmetic may be in the shape of a star, a heart, a flower, or the like, in addition to the shape of a circle, an ellipse, a droplet, and a rectangle.

In the case where the stick cosmetic of this embodiment is used for eyelids, it is preferable that the sectional surface of the stick cosmetic in the direction perpendicular to the longitudinal direction of the stick cosmetic has a diameter or the shortest diameter passing through the center of the sectional surface being from 1 mm to 7 mm. The diameter or the shortest diameter may be 1 mm or longer, more preferably 1.5 mm or longer, and even more preferably 2 mm or more, and may be preferably 6 mm or shorter, more preferably 5 mm or shorter, and even more preferably 4 mm or shorter. According to such a range, it is easy to draw fine lines around the eyes such as the eyelids. In addition, in this embodiment, the length of the cosmetic is preferably from 20 mm to 100 mm.

In the case where the stick cosmetic of this embodiment is used for lips, it is preferable that the sectional surface of the stick cosmetic in the direction perpendicular to the longitudinal direction of the stick cosmetic has a diameter or the shortest diameter passing through the center of the sectional surface being from 1 mm to 7 mm. The diameter or the shortest diameter may be 1 mm or longer, more preferably 1.5 mm or longer, and even more preferably 2 mm or more, and may be preferably 6 mm or shorter, more preferably 5 mm or shorter, and even more preferably 4 mm or shorter. According to such a range, it is easy to draw outlines of the lips. In addition, in this embodiment, the length of the cosmetic is preferably from 20 mm to 100 mm.

It is preferable that a ratio [Length/Diameter] of the length of the stick cosmetic in the longitudinal direction to the diameter of the sectional surface in the direction perpendicular to the longitudinal direction of the stick cosmetic or the shortest diameter passing through the center of the sectional surface is from 4 to 100. The ratio may be preferably 5 or more, more preferably 7 or more, and even more preferably 10 or more, and may be preferably 100 or less, more preferably 50 or less, and even more preferably 30 or less. According to such a range, in the elongated stick cosmetic, the shape retainability when manufacturing or the impact resistance, and the feeling of use, which are the effects of the present invention, are more compatible.

In the sectional surface of the stick cosmetic in the direction perpendicular to the longitudinal direction of the stick cosmetic, it is preferable that a ratio of the area of the inner core to the area of the whole sectional surface is from 0.2 to 0.7. According to such a range, in the elongated stick cosmetic, the shape retainability when manufacturing or the impact resistance, and the feeling of use are more compatible.

The use of the stick cosmetic of this embodiment is not particularly limited, and examples thereof include eye cosmetics such as an eyeliner, an eyebrow pencil, a concealer pencil, and an eye shadow pencil; a lipliner, and the like. Among them, the eye cosmetics in which the smoothness when drawing is easily felt are preferable, and the eyeliner is particularly preferable.

EXAMPLES

Hereinafter, the present invention will be described in more detail with reference to Examples, but the invention is not limited thereto.

Evaluation methods adopted in each Example will be described.

(1) Shape Retainability when Manufacturing

Mold releasability of a double-structured stick cosmetic prepared in the manner described below after cooling was visually determined. The mold releasability were evaluated by three levels of S, A and C.

<Evaluation Criteria>

S: Mold releasability is excellent with sufficient shape retainability

A: There are some scratches on the surface, but the cosmetic can be released.

C: Breakage or collapse occurs when released or it is difficult to release the cosmetic.

(2) Smoothness when Drawing and Long-Lasting Properties

Twenty professional cosmetic evaluation panels used a sample of the double-structured stick cosmetic on the eyelids, and each evaluated smoothness when drawing and long-lasting properties by 5 levels of 1 to 5 points (1-point is the worst, and 5-point is the best). The average point thereof was obtained, and determination was performed on the basis of the following determination criteria.

<Determination Criteria (Average Point of Evaluation Points)>

S: 4 or more

A: 3 or more and less than 4

B: 2 or more and less than 3

C: less than 2

(3) Impact Resistance

The molded stick cosmetic was mounted on a mechanical pencil container, left to stand at 25° C. for 24 hours, then, horizontally dropped from a height of 50 cm 5 times, and was visually determined by 4 levels.

<Evaluation Criteria>

S: There are no abnormalities

A: There are some scratches on the surface of the cosmetic

B: There are a few cracks (the cosmetic can be extruded from the container)

C: There are breakage or bentness (the cosmetic cannot be extruded from the container)

(4) Bulk Hardness

For each of outer layer compositions and inner core compositions, a sample was prepared by filling a screw cap container having a volume of 30 mL with the composition that was melted by heating, and by leaving to stand at 25° C. overnight. The prepared sample was measured in conditions of a pressure-sensitive axis of 1 mm$\phi$, a penetration rate of 6 cm/min, and a penetration depth of 10 mm, by using FUDOH Rheo Meter RT-2002D•D (manufactured by RHEOTECH).

Examples 1 to 8 and Comparative Examples 1 and 2

Preparation of Double-Structured Stick Cosmetic

Respective components of the outer layer compositions shown in Table 1 described below were mixed at respective ratios (% by mass) shown in the same table, and heated and melted to prepare homogeneous outer layer compositions 1 to 8. Next, a stick-shaped inner having a diameter of 1.8 mm was placed inside a tubular mold having an inner diameter of 3 mm and a length of 50 mm, and the gap therebetween was filled with the melted outer layer composition, followed by cooling and solidifying. Next, the stick-shaped inner mold was removed. Separately, respective components of the inner core compositions shown in Table 2 were mixed at respective ratios (% by mass) shown in the same table, and heated and melted to prepare inner core compositions 1 to 3. The obtained melted inner core composition was poured in the cavity obtained by removing the stick-shaped inner mold, and cooled, to thereby prepare a double-structured stick cosmetic (an eyeliner). The prepared double-structured stick cosmetic having a diameter of 3 mm and a length of 50 mm was taken out from the tubular mold, and stored in a container from which the cosmetic can be extruded.

Example 9

A double-structured stick cosmetic having a diameter of 3 mm and a length of 50 mm was prepared in the same manner as in Example 1, except that a stick-shaped inner mold having a diameter of 1.2 mm and a tubular mold having an inner diameter of 2.3 mm and a length of 35 mm were used instead of the stick-shaped inner mold and tubular mold used in Example 1.

The details of each of the components shown in Tables 1 and 2 are as follows.

Alkyl-modified silicone A: BELSIL CM/13526VP (manufactured by Dow Corning Toray Co., Ltd., Product Name, alkyl (C26-28) dimethicone), having a melting point of 43.4° C., in a paste-form at 25° C., and having an alkyl group substituted on a side chain of a polysiloxane chain Alkyl-modified silicone B: BELSIL W3230 (manufactured by Dow Corning Toray Co., Ltd., Product Name, bisstearoxydimethyl silane), having a melting point of 59.8° C., in a solid-form at 25° C., and having an alkyloyl group substituted on both terminals of a polysiloxane chain Acrylic-modified silicone: KP-561P (manufactured by Shin-Etsu Chemical Co., Ltd., Product Name, (acrylate/stearyl acrylate/dimethicone methacrylate) copolymer), having a melting point of 29.7° C., in a semi-solid-form at 25° C., and having an alkyl group and a silicone chain each substituted on a side chain of an acrylic polymer.

TABLE 1

| | | Composition No. | | | | | | | | |
|---|---|---|---|---|---|---|---|---|---|---|
| | | 1 | 2 | 3 | 4 | 5 | 6 | 7 | 8 | 9 |
| Composition | | | | | | | | | | |
| Component (A) | Alkyl-modified silicone A | 8 | 10 | 3 | 13 | 12 | 10 | — | — | — |
| | Alkyl-modified silicone B | — | — | — | — | — | — | 8 | — | — |
| | Acrylic-modified silicone | — | — | — | — | — | — | — | 8 | — |
| Component (B) | Candelilla wax | 6 | 6 | 7 | 4 | 3 | 6 | 6 | 6 | 6 |
| | Polyethylene | 6 | 6 | 7 | 4 | 3 | 5 | 6 | 6 | 6 |
| | Microcrystalline wax | — | — | — | — | — | 5 | — | — | 4 |
| Liquid oil | Diphenyl siloxyphenyl trimethicone | 3 | 1 | 6 | 1 | 1 | 1 | 3 | 3 | 4 |
| Volatile oil agent | Methyl trimethicone | 24 | 22 | 22 | 20 | 18 | 22 | 24 | 24 | 25 |
| Film-forming agent | Trimethyl siloxysilicate | 23 | 22 | 22 | 24 | 24 | 18 | 23 | 23 | 24 |
| Powder | Black iron oxide | 30 | 33 | 33 | 33 | 33 | 33 | 30 | 30 | 31 |
| | Synthetic mica | — | — | — | 1 | 6 | — | — | — | — |
| Property | | | | | | | | | | |
| Bulk hardness (N) | | 0.86 | 0.9 | 1.42 | 0.57 | 0.51 | 0.74 | 1.98 | 1.06 | 0.81 |

TABLE 2

| | | Composition | | |
|---|---|---|---|---|
| | | 1 (solid) | 2 (solid) | 3 (gel) |
| Composition | | | | |
| Component (A) | Alkyl-modified silicone A | 8 | 7 | — |
| Component (B) | Candelilla wax | 3 | 3 | — |
| | Polyethylene | 3 | 4 | 1 |
| Liquid oil | Diphenyl siloxyphenyl trimethicone | 3 | 2 | — |
| | Ethyl hexyl palmitate | — | — | 6 |
| Volatile oil agent | Methyl trimethicone | 24 | 26 | — |
| | Isododecane | — | — | 24 |
| Film-forming agent | Trimethyl siloxysilicate | 26 | 30 | 6 |
| | Polymethyl silsesquioxane | — | — | 9 |
| Thickener | Dextrin palmitate | — | — | 15 |
| Powder | Black iron oxide | 33 | — | 30 |
| | Mica | — | — | 9 |
| | Titanated mica | — | 28 | — |
| Property | | | | |
| Bulk hardness (N) | | 0.30 | 0.38 | 0.10 |

Evaluation results of the double-structured stick cosmetics obtained by combining the outer layer compositions with the inner core compositions are shown in Table 3.

TABLE 3

| | Example | | | | | | | | | Comparative Example | |
|---|---|---|---|---|---|---|---|---|---|---|---|
| | 1 | 2 | 3 | 4 | 5 | 6 | 7 | 8 | 9 | 1 | 2 |
| Composition | | | | | | | | | | | |
| Outer layer composition of Table 1 | 1 | 1 | 2 | 3 | 4 | 5 | 6 | 7 | 1 | 8 | 9 |
| Inner core composition of Table 2 | 1 | 2 | 1 | 3 | 1 | 1 | 1 | 1 | 1 | 1 | 1 |
| Evaluation | | | | | | | | | | | |
| Shape retainability when manufacturing | S | S | S | A | A | A | S | S | S | C | A |
| Smoothness when drawing | S | S | S | A | S | S | S | B | S | S | B |
| Long-lasting properties | S | S | S | S | A | S | A | S | A | S | B |
| Impact resistance | S | S | S | A | S | S | S | B | S | C | C |

TABLE 3-continued

|  | Example | | | | | | | | | Comparative Example | |
|---|---|---|---|---|---|---|---|---|---|---|---|
|  | 1 | 2 | 3 | 4 | 5 | 6 | 7 | 8 | 9 | 1 | 2 |
|  | Property | | | | | | | | | | |
| Hardness ratio (inner/outer) | 0.35 | 0.44 | 0.33 | 0.07 | 0.53 | 0.59 | 0.41 | 0.15 | 0.35 | 0.28 | 0.37 |

As shown in Table 3, it was checked that the double-structured stick cosmetics obtained in Examples 1 to 9 were evaluated as sufficient or even excellent in all of shape retainability when manufacturing, smoothness when drawing, long-lasting-properties, and impact resistance.

What is claimed is:

1. A double-structured stick cosmetic, comprising:
   a solid-form outer layer comprising a first oil composition; and
   an inner core comprising a second oil composition,
   wherein the first oil composition comprises:
      (A) an alkyl-modified silicone having an alkyl group having 16 to 50 carbon atoms and
      (B) a wax in a solid-form at 25° C. other than (A), and
   wherein the second oil composition comprises:
      (B') a wax in a solid-form at 25° C. other than (A) in a content of 0.1% by mass or more and 15% by mass or less based on a total amount of the second oil composition.

2. The double-structured stick cosmetic according to claim 1, wherein component (A) has a melting point of 25° C. or higher and 50° C. or lower.

3. The double-structured stick cosmetic according to claim 1, wherein a mass ratio [(A)/(B)] of component (A) to component (B) contained in the first oil composition is from 0.2 or larger and 1.5 or smaller.

4. The double-structured stick cosmetic according to claim 1, having a diameter of I mm or larger and 7 mm or smaller.

5. The double-structured stick cosmetic according to claim 1, wherein the solid-form outer layer has a bulk hardness of 0.5 N or more and 2.5 N or less.

6. The double-structured stick cosmetic according to claim 1, wherein a ratio of a bulk hardness of the inner core to a bulk hardness of the solid-form outer layer is 0.05 or more and 0.8 or less.

7. The double-structured stick cosmetic according to claim 1, wherein component (A) is an alkyl-modified silicone having an alkyl group having 24 to 28 carbon atoms.

8. The double-structured stick cosmetic according to claim 1, wherein in a sectional surface of the double-structured stick cosmetic in a direction perpendicular to a longitudinal direction of the double-structured stick cosmetic, a ratio of an area of the inner core to an area of a whole sectional surface is from 0.2 to 0.7.

9. The double-structured stick cosmetic according to claim 1, wherein a content of component (A) in the first oil composition is 1% by mass or more and 15% by mass or less based on a total amount of the first oil composition.

10. The double-structured stick cosmetic according to claim 1, wherein the second oil composition comprises:
   (A') an alkyl-modified silicone having an alkyl group having 16 to 50 carbon atoms in a content of 0.1% by mass or more and 15% by mass or less based on the total amount of the second oil composition.

11. A manufacturing method of a double-structured stick cosmetic comprising an inner core and a solid-form outer layer, the method comprising steps of:
   placing a stick-shaped inner mold inside a tubular mold;
   filling a gap between the stick-shaped inner mold and the tubular mold with a first oil composition;
   solidifying the first oil composition;
   removing the stick-shaped inner mold to form the outer layer having a cavity inside;
   filling the cavity with a second oil composition to form the inner core; and
   taking out the double-structured stick cosmetic comprising the inner core and the outer layer from the tubular mold,
   wherein the first composition comprises:
      (A) an alkyl-modified silicone having an alkyl group having 16 to 50 carbon atoms and
      (B) a wax in a solid-form at 25° C. other than (A), and
   wherein the second oil composition comprises:
      (B') a wax in a solid-form at 25° C. other than (A) in a content of 0.1% by mass or more and 15% by mass or less based on a total amount of the second oil composition.

12. The manufacturing method according to claim 11, wherein the first oil composition is heated and melted and then poured to fill the gap, and cooled to be solidified.

13. The manufacturing method according to claim 11, wherein component (A) has a melting point of 25° C. or higher and 50° C. or lower.

14. The manufacturing method according to claim 12, wherein a mass ratio [(A)/(B)] of component (A) to component (B) contained in the first oil composition is from 0.2 or larger and 1.5 or smaller.

15. The manufacturing method according to claim 11, wherein the tubular mold has an inner diameter of 1 mm or larger and 7 mm or smaller.

16. The manufacturing method according to claim 11, wherein the solid-form outer layer has a bulk hardness of 0.5 N or more and 2.5 N or less.

17. The manufacturing method according to claim 11, wherein a ratio of a bulk hardness of the inner core to a bulk hardness of the solid-form outer layer is 0.05 or more and 0.8 or less.

18. The manufacturing method according to claim 11, wherein component (A) is an alkyl-modified silicone having an alkyl group having 24 to 28 carbon atoms.

19. The manufacturing method according to claim 11, wherein in a sectional surface of the double-structured stick cosmetic in a direction perpendicular to a longitudinal direction of the double-structured stick cosmetic, a ratio of an area of the inner core to an area of a whole sectional surface is from 0.2 to 0.7.

* * * * *